(12) United States Patent
Gupta et al.

(10) Patent No.: US 9,528,885 B2
(45) Date of Patent: Dec. 27, 2016

(54) WIRELESS SENSOR FOR ROTATING ELEMENTS

(71) Applicant: Purdue Research Foundation, West Lafayette, IN (US)

(72) Inventors: Lokesh Anilkumar Gupta, West Lafayette, IN (US); Dimitrios Peroulis, West Lafayette, IN (US); Lionel A. Young, Murietta, CA (US)

(73) Assignee: Purdue Research Foundation, West Lafayette, IN (US)

( * ) Notice: Subject to any disclaimer, the term of this patent is extended or adjusted under 35 U.S.C. 154(b) by 396 days.

(21) Appl. No.: 14/194,479

(22) Filed: Feb. 28, 2014

(65) Prior Publication Data

US 2014/0353920 A1    Dec. 4, 2014

Related U.S. Application Data

(63) Continuation of application No. 13/907,624, filed on May 31, 2013, now Pat. No. 9,383,267.

(51) Int. Cl.

| | | |
|---|---|---|
| *G01K 7/38* | (2006.01) | |
| *G01R 33/038* | (2006.01) | |
| *F16J 15/34* | (2006.01) | |
| *G01K 7/36* | (2006.01) | |
| *G01N 25/72* | (2006.01) | |
| *G01R 33/07* | (2006.01) | |
| *G01K 13/08* | (2006.01) | |

(52) U.S. Cl.
CPC .............. *G01K 7/38* (2013.01); *F16J 15/3492* (2013.01); *G01K 7/36* (2013.01); *G01K 13/08* (2013.01); *G01N 25/72* (2013.01); *G01R 33/038* (2013.01); *G01R 33/07* (2013.01)

(58) Field of Classification Search
USPC .......................... 374/152, 171, 184; 318/748
See application file for complete search history.

(56) References Cited

U.S. PATENT DOCUMENTS

| | | | | |
|---|---|---|---|---|
| 6,163,091 A | * | 12/2000 | Wasson .................. | H02K 41/03 310/12.19 |
| 6,528,922 B2 | * | 3/2003 | Lee ......................... | H01R 39/39 310/239 |
| 6,611,078 B1 | * | 8/2003 | Durham ............... | H02K 21/042 310/154.29 |
| 7,893,579 B2 | * | 2/2011 | Rudel .................... | H02K 29/08 310/156.05 |
| 2010/0231213 A1 | * | 9/2010 | Nieuwenhuis ......... | B82Y 25/00 324/252 |
| 2011/0030826 A1 | * | 2/2011 | Bahl ..................... | F16K 31/002 137/803 |

* cited by examiner

*Primary Examiner* — Lisa Caputo
*Assistant Examiner* — Nasir U Ahmed
(74) *Attorney, Agent, or Firm* — Maginot, Moore & Beck LLP

(57) ABSTRACT

A system for measuring a physical characteristic of mechanical face seal includes a permanent magnet and a magnetic sensor. The permanent magnet is affixed to a structure proximate to a bearing surface of the mechanical face seal. The permanent magnet has a magnetic field that decreases as a function of temperature. The magnetic sensor is mounted on the mechanical face seal in a magnetic field sensing relationship with the permanent magnet. The magnetic sensor is configured to generate a voltage signal corresponding to a sensed magnetic field.

20 Claims, 17 Drawing Sheets (a)

(b)

(a)

(b)

(a)

(b)

Figure 4: (a) Measured Vibration spectrum for magnet sensor. (b) Measured vibration spectrum for accelerometer. The magnet sensor acts as displacement sensor similar to a proximity probe while accelerometer measures vibration as equivalent acceleration

WIRELESS SENSOR FOR ROTATING ELEMENTS

This application is a continuation of U.S. patent application Ser. No. 13/907,624 filed May 31, 2013, which is incorporated herein by reference.

FIELD OF THE INVENTION

The present invention relates to condition sensors, and more particularly, to sensors used for diagnostics, conditioning monitoring and/or damage detection in rotating elements.

BACKGROUND OF THE INVENTION

The implementation of damage identification systems in machines is defined as condition monitoring. During their operating lifetime, machines undergo wear and tear due to friction and aging. This wear and tear is primarily located in bearings, seals, etc., and if not detected can lead to catastrophic failures. One such example is bearings in aircraft. To check reliability of rotating components, bearing assemblies are disassembled and thoroughly inspected for degradation at periodic maintenance intervals. This task is expensive and time consuming.

In many industrial applications, the bearing temperatures rise beyond the maximum operating temperature of the lubricants, leading to evaporation. In such conditions, the bearing failure can be hastened. Accordingly, the possibility of unusually high temperatures operation increases the need for frequent disassembly and inspection, thereby increasing maintenance costs.

The maintenance requirements and costs have led to the development of various wired and wireless sensors for on-line condition monitoring of bearings by measuring temperature, vibration, strain, and the like. Monitoring these parameters provides useful information about the bearing. Using such information, a corrective action can be taken before failure of the system. Bearing mountable thermocouple temperature sensors are commercially available and are attached to an outer race (outer diameter structure) of the bearing for temperature monitoring.

More specifically, a typical bearing includes an inner race, which is coupled to a rotating element, an outer race, which is coupled to a stationary element such as a frame, and bearing balls disposed between the inner race and outer race. The inner race can rotate with respect to the outer race upon the bearing balls. The bearing balls are typically supported in the space between the inner race and the outer race by a cage. Such bearings are well known in the art.

As mentioned above, thermocouple temperature sensors have been coupled to the outer race for monitoring temperature conditions in the bearing. The sensors are coupled to the outer race because of the difficulties of connecting circuits and sensors to a rotating element. One drawback to this monitoring method, however, is that it has been shown that the outer race temperature is not reliable indicator of bearing temperature. This can be due, in part, to the fact that the outer race is typically coupled to large metal frame elements that act as a heat sink, quickly dissipating the heat generated within the bearing. As a result, the measured temperature is not always truly reflective of the internal elements of the bearing.

One solution to the issue of inaccuracy of the thermocouple method discussed above has been proposed in U.S. patent application Ser. No. 134/747,433. In that solution, a wireless sensor using an L-C oscillator may be mounted on the inner race or cage of the bearing which communicates inductively with an external sensor circuit. As such, the L-C oscillator may be mounted on the rotating elements such as the inner race or cage because no wires or other circuitry need be attached to the rotating elements. While this solution overcomes issues with the prior art, it is limited to short distances between the L-C oscillator and the external sensor circuit. In addition, metal barriers between the L-C oscillator and the external sensor circuit can disrupt the sensor signal.

Accordingly, there is a need for a wireless sensor for condition monitoring in a rotating bearing element that avoids the problems of the prior art.

In addition to ball bearings, mechanical face seals require similar condition monitoring. Mechanical face seals are assemblies that provide a sealing surface for rotating parts having internal lubrication. Mechanical face seals are typically made up of silicon-carbide and carbon. In case of lack of lubrication, or thin fluid film rupture between seal stator and rotor, the sliding surfaces may run dry resulting in increased friction and higher seal face heat generation. This may result in increased fluid leakage and premature seal failure. In such cases, excessive seal face wear may occur. As a result, the seal face may become wavy, tapered, or heavily grooved and in the case of liquid hydrocarbon type fluids, coke deposits and fluid evaporation due to excessive heat etc. may be observed. It has long been established that seal face temperature is a good indicator of operation. Thus, it is essential to monitor seal interface conditions.

In prior art designs, a thermocouple was attached to the seal stator for condition monitoring. This method is often undesirable as it is difficult to mount wired sensors in millimeter-size spaces that exist between mechanical seal and a rotating shaft. In addition, when the mechanical seal is replaced after its useful life, wired sensors are difficult to replace without disconnecting the signal processing circuitry due to the fact that thermocouples are typically glued to the seal stator.

SUMMARY OF THE INVENTION

At least some embodiments of the present invention addresses the above needs, as well as others, by providing a physical condition sensor that includes a permanent magnet and a magnet sensor.

A first embodiment is a system for measuring a physical characteristic of a bearing that includes a permanent magnet and a magnetic sensor. The permanent magnetic is coupled to at least a portion of a bearing, and has a magnetic field that changes as a function of the physical characteristic. For example, the permanent magnet has a magnetic characteristic that changes as a function of temperature. The magnetic sensor is operably disposed in a magnetic field sensing relationship with the permanent magnet, and is configured to generate a voltage signal and/or current signal corresponding to a sensed magnetic field.

A second embodiment is a system for measuring a physical characteristic of mechanical face seal that includes a permanent magnet and a magnetic sensor. The permanent magnet is affixed to a structure proximate to a bearing surface of the mechanical face seal. The permanent magnet has a magnetic field that decreases as a function of temperature. The magnetic sensor is mounted on the mechanical face seal in a magnetic field sensing relationship with the permanent magnet, the magnetic sensor configured to generate a voltage signal corresponding to a sensed magnetic field.

DETAILED DESCRIPTION

Figure 1:
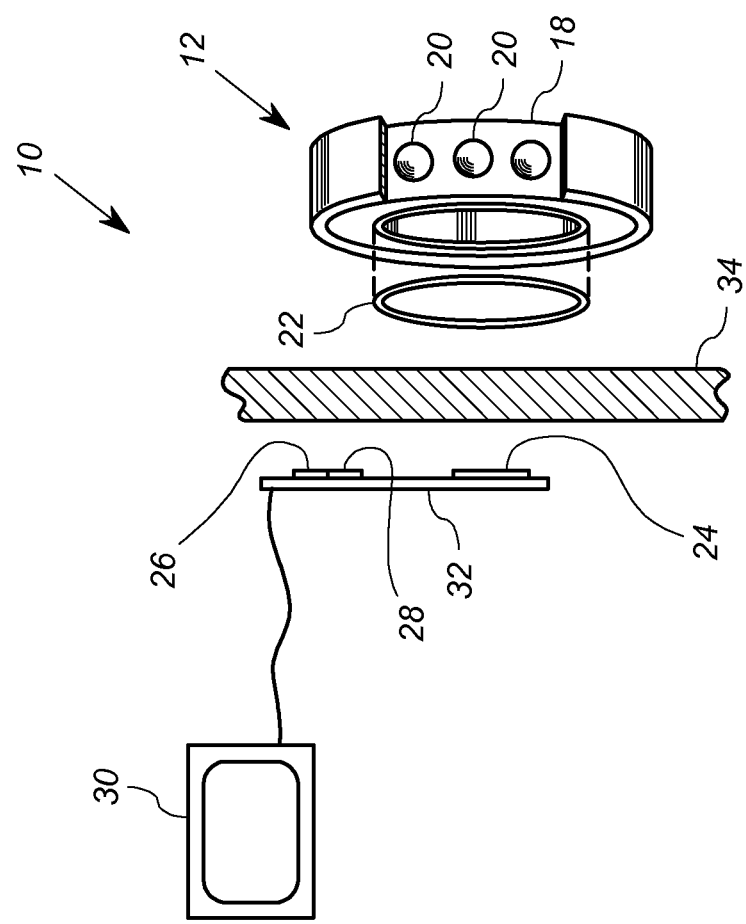
FIG. 1 shows an exploded assembly view and schematic diagram of an arrangement for measuring at least one physical characteristic of a bearing.

FIG. 1 shows an arrangement 10 for measuring at least one physical characteristic of a bearing 12. The arrangement 10 includes the bearing 12, a measurement system 11 and a display 30. The measurement system 11 includes a permanent magnet 22, a magnetic sensor 24, a processing circuit 26, and a memory 28. In general, the permanent magnet 22 and magnetic sensor 22, 24 cooperate to form a wireless sensor 22, 24. In the arrangement 10 of FIG. 1, the bearing 12 is part of a larger structure or machine, not shown, but which includes a metallic wall or device 34 interposed between the magnetic sensor 24 and the bearing 12. In general, the metallic wall or device 34 provides structural, protective, or other function to the bearing 12 and/or to the larger structure to which the bearing 12 is mounted.

In this embodiment, the bearing 12 is a ball bearing that includes an inner race 14, and outer race 16, a cage 18 and a plurality of balls 20. In general, the cage 18 and the plurality of balls 20 are disposed between the inner race 14 and the outer race 16. The cage 18 provides a structure in which the balls 20 are trapped, but yet can rotate. As is known in the art for a typical ball bearing, the inner race 14 and the outer race 16 are constructed such that they can rotate with respect to each other. To this end, each of the inner race 14 and the outer race 16 includes a bearing surface against which the balls 20 bear. Such devices are known in the art, and may include, by way of non-limiting example the model 6012 bearing available from Torrington.

The permanent magnetic 22 is affixed to and coupled to at least a portion of a bearing 12. In this embodiment, the permanent magnet 22 is coupled to a rotating part of the bearing 12, such as the inner race 14 or the cage 18. The permanent magnet 22 has a magnetic field that decreases as a function of temperature. To this end, the permanent magnet 22 can be formed at least in part from Neodymium, such as NdFeB. In other embodiments, the permanent magnet can be formed of a material selected from the group of Alnico, Ceramic, and SmCo. Coupling the permanent magnet 22 to the inner face 14 or the cage 18 is advantageous because the temperature of the bearing 12 is more accurately measured from these locations. The permanent magnet 22 is affixed to the bearing 12 via magnetic attraction and/or an adhesive.

The magnetic sensor 24 is operably disposed in a magnetic field sensing relationship with the permanent magnet 22, and is configured to generate a voltage and/or current signal corresponding to a sensed magnetic field. To this end, the magnetic sensor 24 may suitably be a Hall Effect sensor. Alternatively, the magnetic sensor 24 may include or comprise a magneto-resistance elements that change in resistance due to magnetic fields in thin semiconductor film. Hall Effect sensors have a more linear response as a function of magnetic field, while magneto-resistance elements can have greater sensitivity. In this embodiment, the magnetic sensor was a model A1395 Hall Effect sensor from Allegaro, which has a size of about 6 mm².

The magnetic sensor 24 in this embodiment is mounted on a circuit board 32, along with the processing circuit 26 and the memory 28. The processing circuit 26 is a circuit that is configured to obtain sensor output signals from the magnetic sensor 24 and store information representative of the sensed magnetic field in the memory 28. In some embodiments, the processing circuit 26 is configured to generate a value representative of temperature based on the output of the magnetic sensor 24. To this end, the processing circuit 26 may suitably include an A/D converter, amplifiers, filters, a digital processor and other related circuitry. The memory 28 may suitably be a non-volatile or volatile data memory.

The processing circuit 26 is also operably coupled to provide processed information representative of the magnetic sensor measurements (i.e. converted to temperature information) to a display 30. The display 30 may be part of remote computer system, or a system within the larger structure in which the arrangement 10 is located. For example, if the bearing 12 is a bearing in an aircraft, the display 30 may suitably be a display within the cockpit of the aircraft. The display 30 may alternatively be a part of a remote diagnostic computer.

In normal operation, the inner race 14 of the bearing 12 rotates, in many cases at a high speed. By way of example, the inner race 14 may be fixedly coupled to a rotating shaft such as that of a helicopter rotor, not shown, while the outer race 14 is fixedly coupled to a relatively stationary element such as the helicopter frame, which can included the metallic sheet 34. The magnetic sensor 24, which is located close enough to the permanent magnet 22 to sense its magnetic field, generates a sense signal having a voltage (or current) that is representative of the detected magnetic field from the permanent magnet 22. The magnetic sensor 24 provides the sense signal to the processing circuit 26. The processing circuit 26 periodically samples the sense signal and converts the sampled sense signal into a signal representative of the magnetic field, and preferably temperature. To this end, the magnetic characteristics of the permanent magnet 22 change as a function of temperature. The processing circuit 26 may convert sensed values into a temperature value based on a programmed linear relationship between sensor voltage (or current) and temperature, which can be determined experimentally. Alternative the processing circuit 26 may convert sensed values using temperature/magnetic field correlation data stored in the memory 28. The sensed temperature information generated by the processing circuit 26 may be stored in the memory 28 and/or provided to the display 30, sometimes via other processing circuits, not shown. In some cases, the processing circuit 26 filters the converted samples to obtain a filtered temperature value. The filtering operation may include simple averaging or other techniques for avoiding spurious noise.

As the inner race 14 rotates, friction heat will be generated by the bearing surfaces of the balls 20, the inner race 14, the outer race 16 and the cage 18. As a result of the increased heat, the permanent magnet 22 also increases in temperature through heat conduction from the inner race 14 and/or cage 18. The increase in temperature causes the magnetic field of the permanent magnet 22 to change. The magnetic sensor 24 continues to generate sense signals, which also change due to the change in the magnetic field of the permanent magnet 22. The processing circuit 26 processes and stores the sampled sense signal, and stores and/or provides for display the temperature information, which now has an increased value.

It will be appreciated that the processing circuit 26 may be configured to provide alarm signals or the like if the filtered, sensed temperature value exceeds a predetermined threshold. The alarm can be used to indicate wear on the bearing 12, and/or provide predictive information regarding potential failure. As the bearing 12 wears, it will exhibit higher temperature due to increased friction. At some level the operating temperature as detected by the arrangement 10 will be consistently at an elevate level, indicating the need for maintenance.

It will be appreciated that one of the advantages of the embodiment described above is that part of the wireless sensor, namely the permanent magnet 22, is directly coupled to a rotating part, which more accurately senses or detects the heat within the bearing 12. Moreover, the permanent magnet 22 can convey the detected heat (in the form of its variable magnetic field) wirelessly and through metallic or steel structures such as the metallic layer 34. Thus, the permanent magnet 22 and magnetic sensor 24 allow for detecting temperature and/or wear on bearings even in difficult environments when the permanent magnet 22 and the magnetic sensor 24 must be separated by intervening structures.

In addition to temperature, the arrangement 10 may also be used to measure vibration in the bearing 12. To this end, it has been observed that vibration in the rotating element to which the permanent magnet 22 is attached, such as the inner race 14, will cause periodic fluctuations in the distance and/or angle between the permanent magnet 22 and the magnetic sensor 24. These fluctuations, which correspond directly to the vibration, cause corresponding changes in the magnetic field sensed by the magnetic sensor 24. Accordingly, in at least some embodiments, the processing circuit 26 is configured to process the incoming sense signal to identify the periodic component of the signal that is due to vibration.

Figure 15:
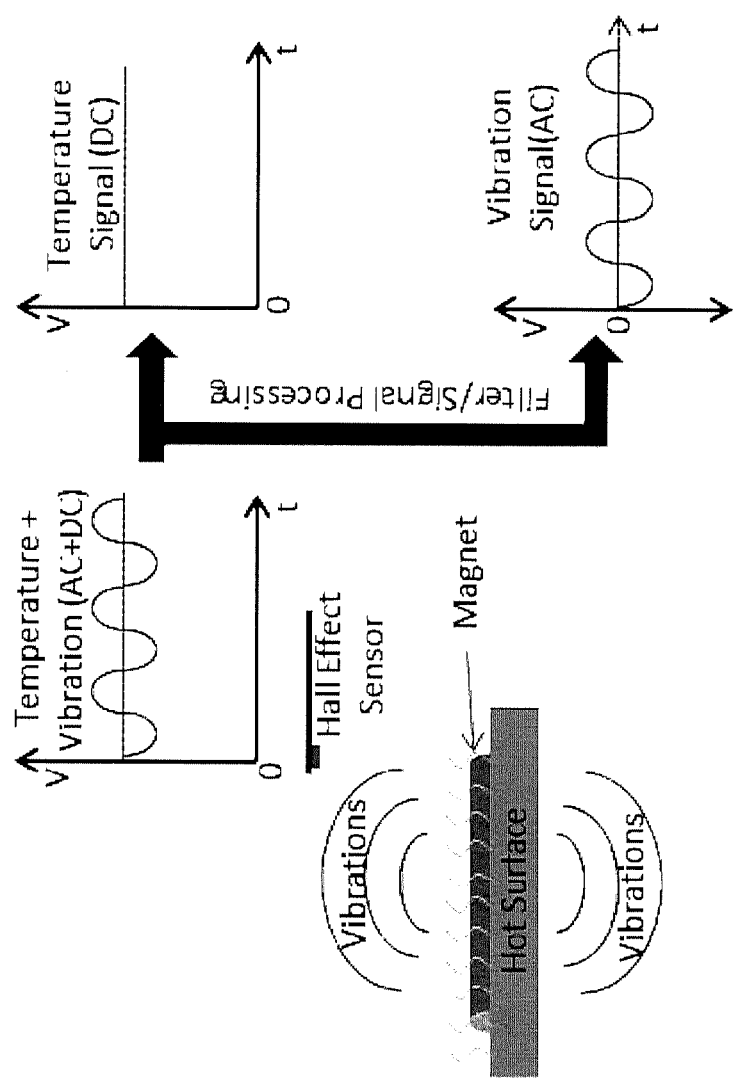
FIG. 15 shows a flow diagram of the theory of operation of the arrangement of FIG. 2.

In particular, the processing circuit 26 can separate the portions of the sensed signal due to vibration from the portions of the sensed signal due to heat using filtering. Heat-induced components of the magnetic field are relatively low in frequency, because of the time constant associated with heating and cooling bearing components and magnetic elements. Moreover, in many cases, the temperature is at steady state for a long time, resulting in a flat voltage level produced by the magnetic sensor 24. By contrast, the vibration-induced component of the sensed signal will be a periodic, relatively high frequency signal. The period of the vibration component corresponds directly to the periodicity of the vibration. The processing circuit 26 may readily divide these two components using digital or analog filtering, as well as using other methods. FIG. 15, by way of example, shows a theory of operation of this embodiment.

Figure 2:
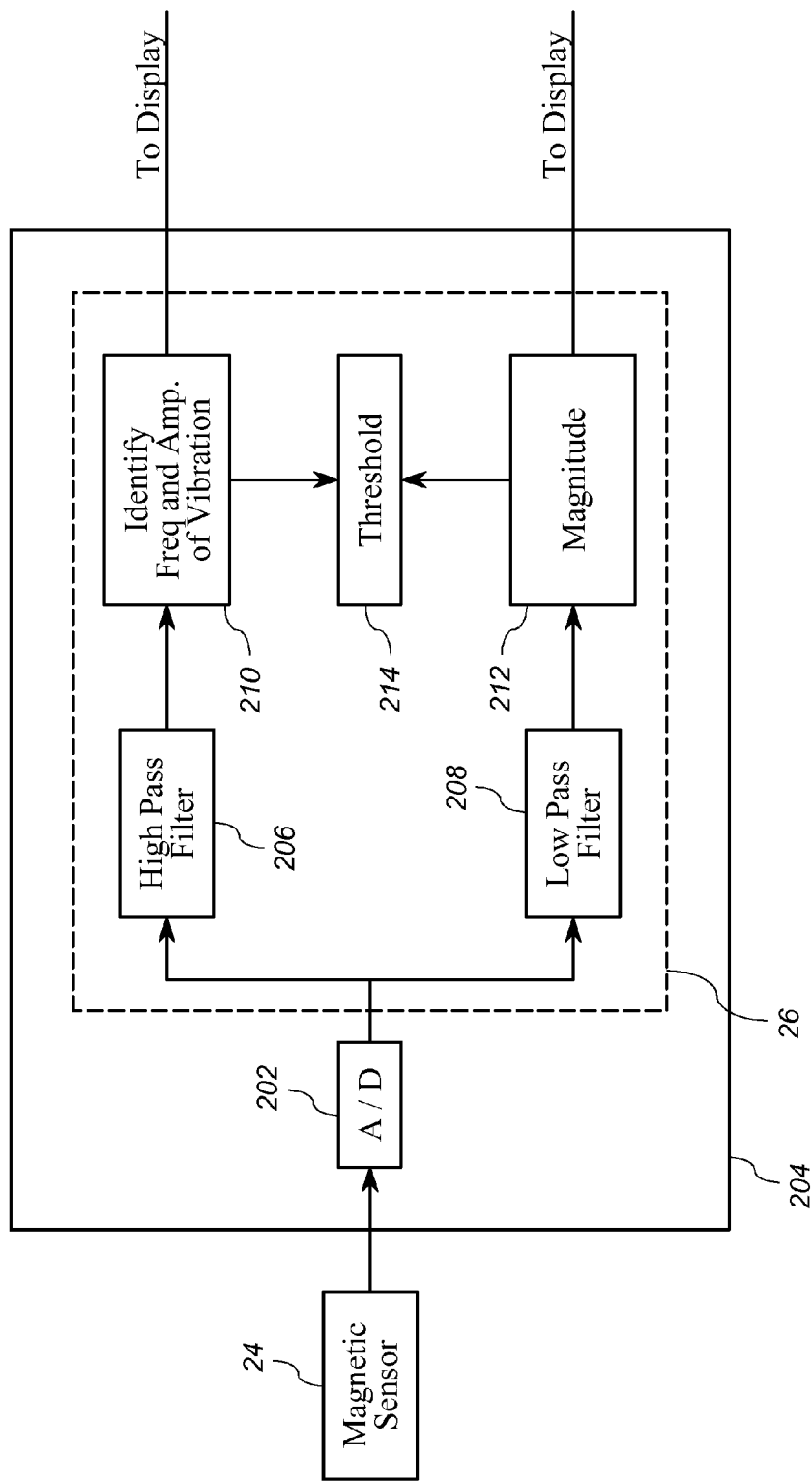
FIG. 2 shows a schematic block diagram of a processing circuit that may be used in the arrangements of FIGS. 1 and/or 5.

FIG. 2 shows a schematic block diagram of an example of a processing circuit 26 that is configured to obtain vibration and temperature measurement values from a sensed signals generated by the magnetic sensor 24 of FIG. 1. The processing circuit 26 includes an A/D converter 202 and a digital processor 204. It will be appreciated that the A/D converter 202 and the digital processor 204 may be discrete elements, or may be integrated into a single chip. The A/D converter 202 is operably coupled to receive the sensed signal from the magnetic sensor 24 of FIG. 1. The A/D converter 202 is configured to sample the sensed signal to generate a sequence of sample values. The sampling rate should substantially exceed the range of expected vibration frequencies. To this end, the sampling rate should be at least 30 samples/sec.

The A/D converter 202 is further operably coupled to provide the sampled sense signal to the digital processor 204. In general, the digital processor 204 determines identifies a portion of the sensed signal attributable to the effect of heat on the magnetic field of the permanent magnet 22 as sensed by the magnetic sensor 24, and identifies a portion of the sensed signal attributable to vibration of the permanent magnet 22 as sensed by the magnetic sensor 24. To this end, in the embodiment described herein, the digital processor 204 includes a digital high pass filter 206 and a digital low pass filter 208. The digital high pass filter 206 has a cut-off frequency that is designed to eliminate any low frequency signal changes, which are largely attributable to temperature changes. The cut-off frequency, however, should not be so high that signal components due to low frequency vibrations are filtered out. Thus, for example, the digital high pass filter 206 may suitably have a cut-off frequency of 1 Hz to 100 Hz or more. The low pass filter 208 should, conversely, have a cut-off frequency that filters out the portion of the sensed signal due to factors other than temperature, such as vibration. To this end, the low pass filter 208 may suitably have a cut-off frequency of 1 Hz to 100 Hz.

The digital processor 204 further includes a first signal analysis function 210 that is operably coupled to receive the high-pass filtered digital sense signal from the high pass filter 206. The first signal analysis function 210 is configured to determine at least one frequency component of the signal and its amplitude. The first signal analysis function 210 may suitably provide the determined frequency and amplitude to the display 30 of FIG. 1, the memory 28 of FIG. 1, and/or to a further processing function 214 that determines whether or not the value indicates a need for maintenance or repair. For example, the further processing function 214 may suitably compare the amplitude of the high frequency component of the sensed signal to an amplitude threshold. If the sensed amplitude exceeds the threshold, then the processing function 214 may provide a notification signal to other circuits such as the display 30 of FIG. 1. The first signal analysis function 210 and the further processing function 214 may be implemented through routine programming.

The digital processor 204 also includes a second signal analysis function 212 that is operably coupled to receive the low-pass filtered digital sense signal from the low pass filter 208. The second signal analysis function 212 is configured to determine the amplitude of the steady state voltage of the low-pass filtered digital sense signal. The second signal analysis function 210 may suitably provide information representative of the determined amplitude to the display 30 of FIG. 1, the memory 28 of FIG. 1, and/or to the further processing function 214. The further processing function 214 is further configured to determine whether or not the value indicates a need for maintenance or repair. For example, the further processing function 214 may suitably compare the amplitude of the low frequency component of the sensed signal to another amplitude threshold. If the sensed amplitude exceeds the threshold, then the processing function 214 may provide a notification signal to other circuits such as the display 30 of FIG. 1. The second signal analysis function 212, like the further processing function 214 may be implemented through routine programming. The second signal analysis function 212 or the further processing function 214 may also be configured to convert the sensed steady state voltage level of the low frequency component of the sense signal to an actual temperature value based on a conversion function or a table stored in the memory 28.

It will be appreciated that instead of arrangement of the digital processor 204 of FIG. 2, the digital processor 204 may instead include or comprise a spectrometer function or element that provides a full frequency analysis of the digitized sense signal. The output of the spectrometer is data representative of the amplitude of each of a spectrum of frequencies. The DC or other low frequency signal response is also identified by the spectrometer.

Thus, the wireless sensor 22, 24 of FIG. 1 may be used to sense physical characteristics such as vibration and temperature in rotating bears in a way that has improved accuracy, and does not require complicated connection schemes.

It will be appreciated that a preferred embodiment, the wireless sensor 22, 24 is configured to detect the vibration of a rotating device due to the operation of the rotating device. To this end, the permanent magnet 22 should be affixed to an element that is influenced by such rotation more than the element to which the magnetic sensor 24 is affixed. If both elements 22, 24 vibrate uniformly, the vibration will not be detected. At least one element (i.e. the magnet 22) should be affixed on or near the rotating device (i.e. on the inner race 14) such that vibrations in the rotating device translate to the permanent magnet 22. The magnet sensor 24, however, should be affixed to a frame (i.e. of the machinery or vehicle) or other element at a location where at least some of the vibration due to rotation of the rotating device does not translate, or at least translates to a significantly lesser extent.

The concepts of FIG. 2 have been implemented in one working example using a Micronas HAL 825 Hall Effect sensor 24 to measure temperature and vibration-induced change in magnetic field of permanent neodymium magnet 22. The Hall Effect sensor 24 was programmed to its highest sensitivity of 40 mV/Gauss. Neodymium magnets are commercially available in various sizes and shapes. They are further subdivided into multiple grades depending on temperature rating, energy content, coercivity. In this example, a semi-cylindrical shaped 4.4-mm diameter, 9.5-mm length L38EHT magnet was employed as the magnet 22. Such a magnet is polarized along its length with temperature rating of 200° C., coercivity of 2388 KOe and B—H product of 38 MGOe.

In an experiment, the semi-cylindrical magnet 22 was attached to an aluminum holder. The processing circuit 26 was carried out as discrete components analogous to those of FIG. 2. The aluminum holder served the purpose of maintaining uniform temperature across the magnet volume. The holder was attached to the hot plate using double-sided tape. A thermocouple was attached to the holder as shown for reference temperature measurement. The Hall Effect sensor 24 was mounted on a small PCB. In typical test system the magnet would be placed on a vibrating hot body; however, in this case it is difficult to introduce vibrations on the magnet directly due to size and weight limitations of the hot plate. Hence, to demonstrate simultaneous measurement of temperature and vibration, the Hall Effect sensor PCB is attached to a piezoelectric actuator, not shown. In other words, the sensor 24 was vibrated to simulate the vibration of the magnet 22. This unique assembly was mounted on a Z-axis setup at a distance of 13-mm from the magnet's south pole. The Hall Effect sensor 24 measured the vertical component of the magnetic field lines originating at the magnet's south pole. The piezoelectric actuator was connected to a signal generator for excitation. When the piezoelectric actuator was excited at certain frequency, the position of the Hall Effect sensor 24 changed periodically with respect to the magnet 22. The vibrations were detected by capturing the AC component in the Hall Effect sensor 24 output on a spectrum analyzer, not shown, but which performed the first frequency analysis function 210 of the processing circuit 26. The Hall Effect sensor output was connected to spectrum analyzer through a large DC blocking capacitor (e.g. a crude analog form of the high pass filter 206), for vibration signal measurement. This output of the Hall Effect sensor 24 was also connected to a multi-meter, which formed the second frequency analysis function 212, without the DC block, for temperature measurement. A standard accelerometer with sensitivity if 100 mV/G was attached to the Z-axis setup for reference vibration measurements. The data was recorded on a PC using LabVIEW.

The hot plate was cycled from 10° C. to 90° C. with rise time, fall time and constant temperature time of 40 minutes each. The piezoelectric actuator had a rated displacement of 315 μm at ±90 Vp-p excitation. For this setup, the excitation voltage from function generator was ±10 Vp-p resulting in estimated tip displacement of 35 μm at resonance. Although the specified resonant frequency of the stand-alone piezoelectric actuator was 272 Hz, this resonant frequency was reduced to approximately 200 Hz as the beam was loaded with the Hall Effect sensor PCB.

Figure 16:
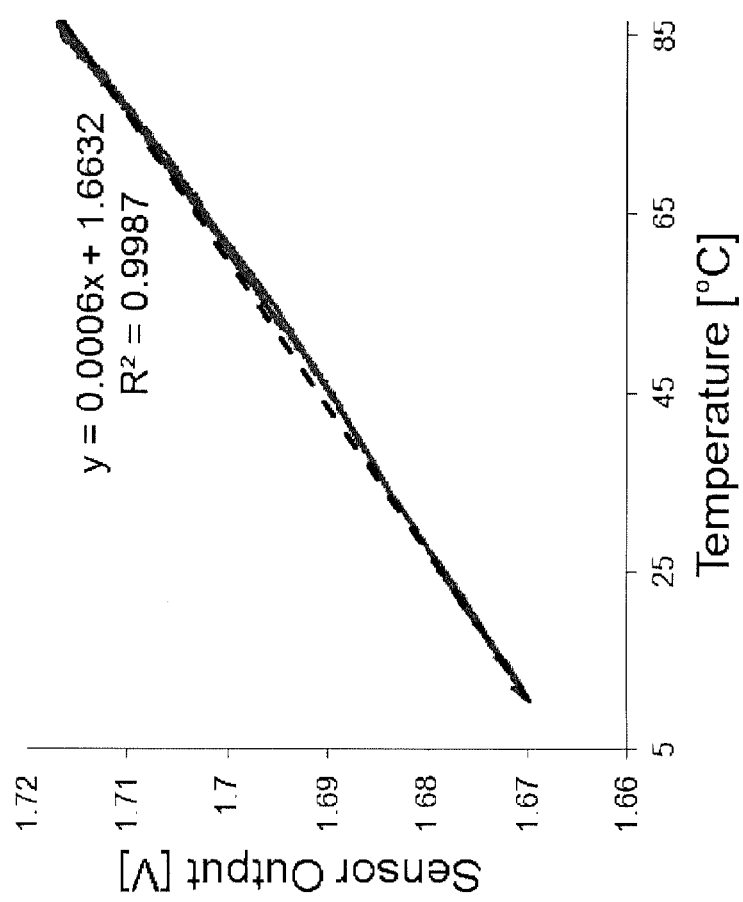
FIG. 16 shows the Hall Effect sensor output vs. temperature from 10° C. to 85° C. for an exemplary test set-up of the arrangement of FIG. 1.
Figures 17A, 17B:
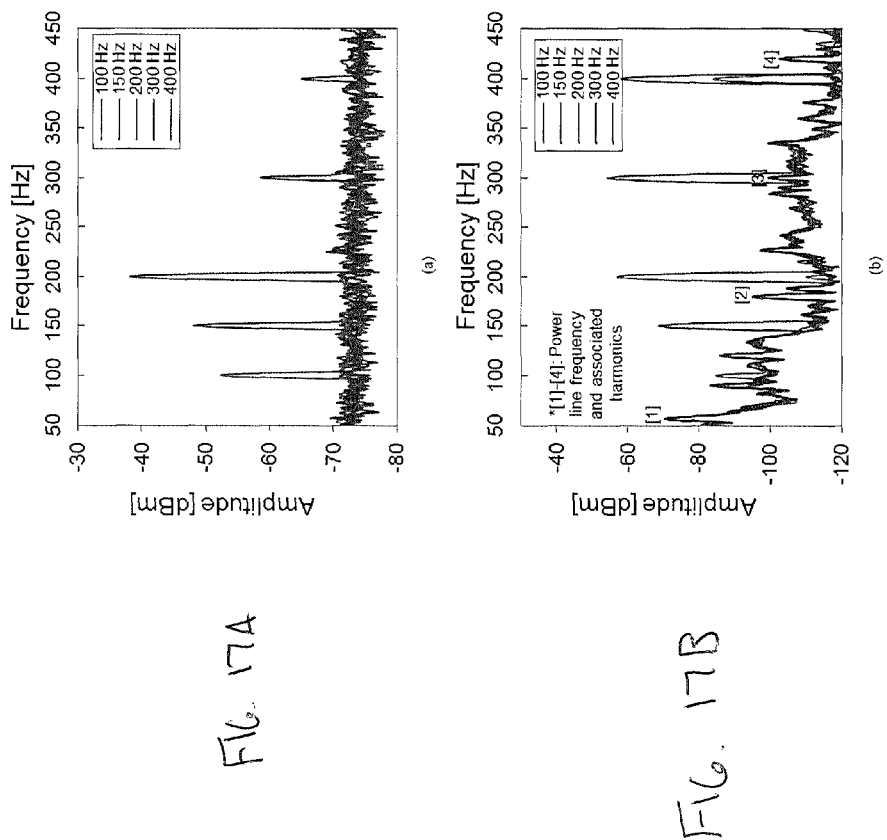
FIGS. 17A and 17B show a vibration measurement spectrum for, respectively, the magnet sensor of the arrangement of FIG. 1.

The piezoelectric actuator was subjected to multiple frequencies to obtain the test data. FIG. 15 shows the Hall Effect sensor output vs. temperature from 10° C. to 85° C. for this exemplary arrangement of the arrangement 10 of FIG. 1. The measurements show linear trend with curve fit value of greater than 98%. FIGS. 16A and 16B show a vibration measurement spectrum for, respectively, the magnet sensor 22, 24, and the reference accelerometer, under the conditions with the piezo-electric actuator simulating vibrations at each of 100 Hz, 150 Hz, 200 Hz, 300 Hz and 400 Hz. The magnet sensor 22, 24 was able to detect all the frequencies applied to the piezoelectric actuator with high accuracy in comparison to accelerometer. An important point to be noticed in the FIGS. 16A and 16B is the amplitude of the signals at various frequencies. The magnet sensor 22, 24 acts as displacement sensor, resulting in measured amplitude being proportional to the actual displacement of the Hall effect sensor with respect to the magnet. Hence, a large amplitude signal is observed at the resonant frequency of 200 Hz. While accelerometer measures same frequency components, the measured amplitude is proportional to acceleration at the fixed end of the piezoelectric actuator on the Z-axis setup. The accelerometer spectrum shows various power line frequencies and associated harmonics with the frequency dependent noise floor varying from −80 dBm to −120 dBm. These line frequencies and noise floor variations are probably introduced by the accelerometer signal processor. These frequencies are absent in the magnet sensor output.

Accordingly, a wireless sensor capable of measuring vibrations and temperature simultaneously using permanent magnet 22 and magnetic sensor 24 has been successfully demonstrated. The temperature measurements showed linear trend up to 85° C. for a magnet-Hall Effect sensor 24 distance of 13 mm. Furthermore, the magnet sensor 22, 24 detected all the vibration frequencies, as also detected by an accelerometer with high degree of congruity.

Further detail regarding the theory and various tests of the sensor combination 22, 24 is provided below in connection with FIGS. 3-9B.

In general, the wireless sensor 22, 24 represents the first wireless temperature sensor that can operate through thick metal sheets. This is due to the fact that permanent magnets have a specified temperature coefficient. In other words, the magnetic field decreases with an increase in temperature. If this change in the magnetic field is detected, using sensors such the Hall Effect sensor 24 or magneto resistive elements at a fixed distance, then temperature can be measured remotely. It is understood that permanent magnets affect materials with high permeability ferrous metals e.g., iron, nickel and cobalt. The magnetic field is dispersed by these materials and field lines cannot pass through them. However, for materials like austenitic stainless steel, aluminum, copper etc. the combination of the permanent magnet 22 and the Hall Effect sensor 24 can be used for thick metal sheets (e.g. metal element 34), as the magnetic field lines are not affected by the presence of these metals. As discussed above, a first embodiment presents a temperature sensor 22, 24 using the combination of a ring shaped permanent neodymium rare earth magnet 22 and Hall Effect sensor 24 for bearing inner race 14 temperature measurement.

Figure 3:
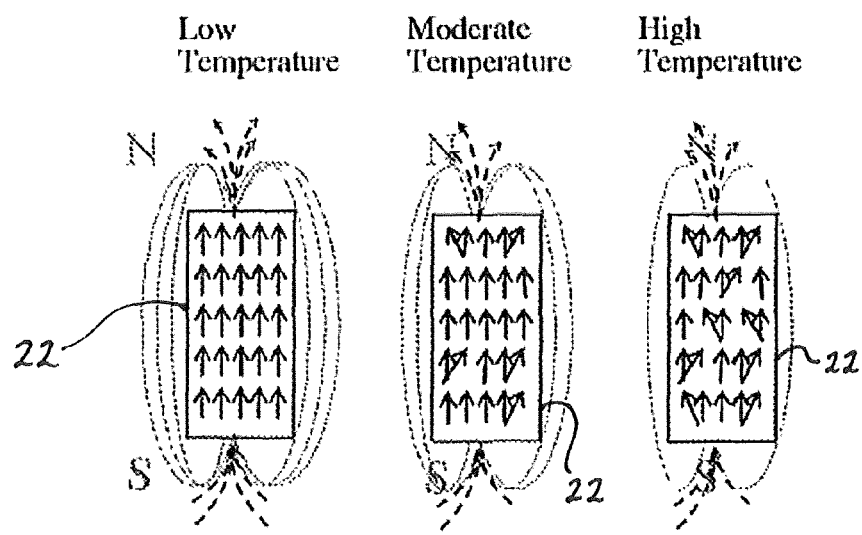
FIG. 3 shows a representative diagram of magnetic domains in a permanent magnet under various temperature conditions.

The fundamental principle behind the change in magnetic field is the change in microscopic magnetic domains due to temperature. In a permanent magnet, the domains are made up of $10^{17}$ to $10^{21}$ atoms of ferrous materials. These domains are randomly oriented when the magnet is fabricated. When the magnet is subjected to an external magnetizing field, the domains align along the direction of the external magnetic field, thus resulting in a permanent magnet. At elevated temperatures the magnetic domain orientation starts to become random, thus magnets start losing field strength. An inverse effect is observed at lower temperatures with magnetic domains aligning along the direction of the poles. These effects are illustrated in FIG. 3. As shown, the arrows representing domains are aligned at low temperatures with higher number of field lines traveling from N to S pole. At higher temperatures some domains have random orientation, thus reducing the number of field lines traveling from N to S poles. For certain temperature ranges, this change in magnetic domains is reversible. This temperature range depends on the type of magnet, its geometry and material composition. Various magnets like Alnico (Aluminum, Nickel, Cobalt), Ceramic, NdFeB (Neodymium, Iron, Boron), SmCo (Samarium, Cobalt) are commercially available in various size and shapes.

These magnets are further classified in multiple grades depending upon there chemical composition and properties like temperature coefficient, energy content (B—H product), maximum operating temperature etc. Table I gives a comparison of various magnet properties. Neodymium magnets have the highest energy product with high coercivity, i.e. these magnets cannot be easily demagnetized. They also have a high temperature coefficient that makes them a good choice for temperature sensing applications. These magnets have Curie temperature of up to 300° C. and an operating temperature range up to 200° C. depending on the grade of magnet. For this application, N-42 grade neodymium magnet was used with temperature coefficient of 0.11%/° C. The numerical '42' in the magnet grade notation represents the B—H product of a given magnet. For sensing higher temperatures, samarium cobalt rare earth magnets can be used as they have Curie temperature of 550° C., operating temperature range of up to 300° C. and temperature coefficient of 0.04%/° C.

TABLE I

TABLE SHOWING COMMON PROPERTIES OF VARIOUS MAGNETIC MATERIALS

| Magnet Type | Energy Product MGOe | Coercivity (kOe) | Maximum Temp. (° C.) | Temp. Coeff. (%/° C.) |
| --- | --- | --- | --- | --- |
| NdFeB | 42 | 30 | 200 | −0.11 |
| SmCo | 30 | 25 | 350 | −0.04 |
| AlNiCo | 10 | 2 | 550 | −0.02 |
| Ceramic | 4 | 2 | 300 | −0.2 |

As discussed above, Hall Effect sensors are based on the Hall Effect observed in semiconductor materials while magneto-resistance elements show change in resistance due to magnetic fields in thin semiconductor film. Hall Effect sensor output is highly linear with change in magnetic field as compared to magneto-resistive elements and responds differently depending on the polarity of the magnet. Hall Effect sensors have limited sensitivity compared to magneto-resistive elements. In this application linearity is a parameter of interest as changes in magnetic field with temperature is a non-linear function.

Sensor Implementation and Characterization

A. Effect of Distance Between Magnet and Hall Effect Sensor

In the embodiment described above in connection with FIG. 1, a ring-shaped magnet 22 was selected with dimensions about 69.5 mm outer diameter and about 63.5 mm inner diameter with a thickness of about 6.35 mm. The sensor was implemented on commercially available SKF 6012-2RSJEM bearing 12. The magnet 22 had dimensions closely matching the inner race 14 of the bearing 12. The bearing 12 was constructed of ferrous material allowing the magnet 22 to be attached to the bearing 12 without any adhesive and was poled through thickness (i.e. each pole was on opposite faces of the ring). As the Hall Effect sensor 24 was sensitive to change in magnetic poles, this construction ensured a single pole always faced the Hall Effect sensor 24. The combination of the ring magnet 22 and the ferrous bearing 12 formed a large magnet which assisted in increasing the volume occupied by the magnetic field lines and increased the interaction of the field lines with the Hall Effect sensor 24 at larger distance on the order of few centimeters. The uniform thickness of the ring shaped magnet 22 ensured that the distance between the magnet 22 and the Hall Effect sensor 24 remained constant thus, the Hall Effect sensor output 24 responded to in magnetic field change due to the bearing temperature. The uniform thickness and ring shape also assist in mounting by minimizing the need for balancing the bearing as two ring shaped magnets can be used on both sides in case the bearing is mounted vertically in the machine. The ring shaped magnet 22 and SKF bearing 12 are shown in FIG. 1, discussed above.

Figure 4:
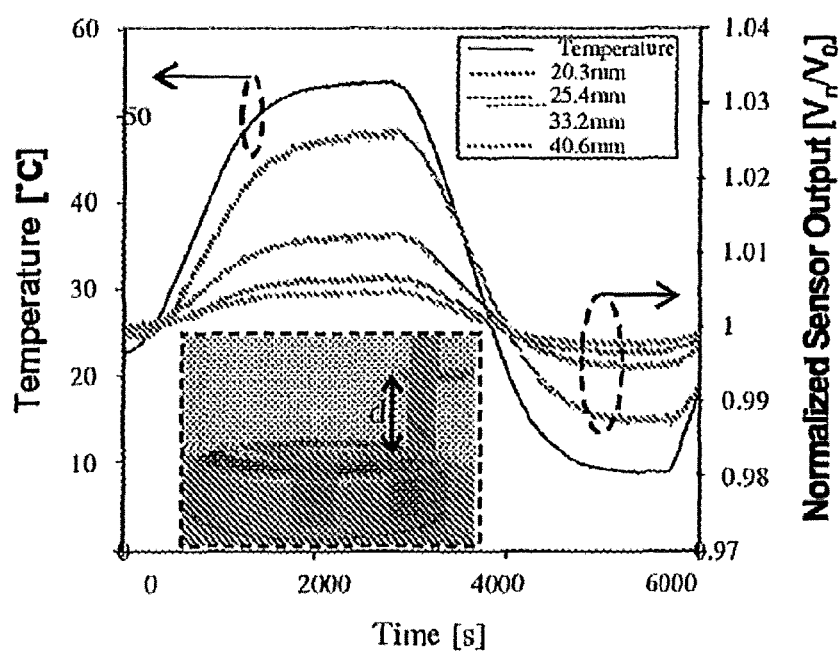
FIG. 4 shows temperature cycling results for four distances between the Hall Effect sensor and the magnet.

In a test configuration, the magnet 22 with the bearing 12 was horizontally attached to a hot-cold plate using thin double-sided adhesive tape. A thermocouple was placed close to the magnet for reference temperature measurement. This test cannot be performed using normal ceramic laboratory hot plates, as these hot plates use heating coils which are magnetic and affect the measurement. Accordingly, a TECA hot-cold plate based on Peltier effect was used: hence no magnetic field was generated by the hot plate. The Hall Effect sensor 24 was soldered on a printed circuit board and mounted on a variable Z-axis setup. The setup was subjected to temperature cycling from 0° C. to 75° C. (Hot plate surface temperature). The data from the thermocouple and the Hall Effect sensor were logged using LABVIEW program and a PC. In this test, the effect of distance variation between magnet and the Hall Effect sensor on temperature measurement was characterized. FIG. 4 shows temperature cycling results for four distances between the Hall Effect sensor and the magnet. The Hall Effect sensor output shape was similar to the temperature curve. Specifically, FIG. 4 shows normalized sensor output and bearing temperature vs. time for various distances. The setup was subjected to temperature cycling for 1.6 hrs. The sensor output followed the temperature plot with some hysteresis. The sensor output readings were normalized with respect the sensor output at room temperature for respective distances as the sensor output reduced with distance.

Figure 5A:
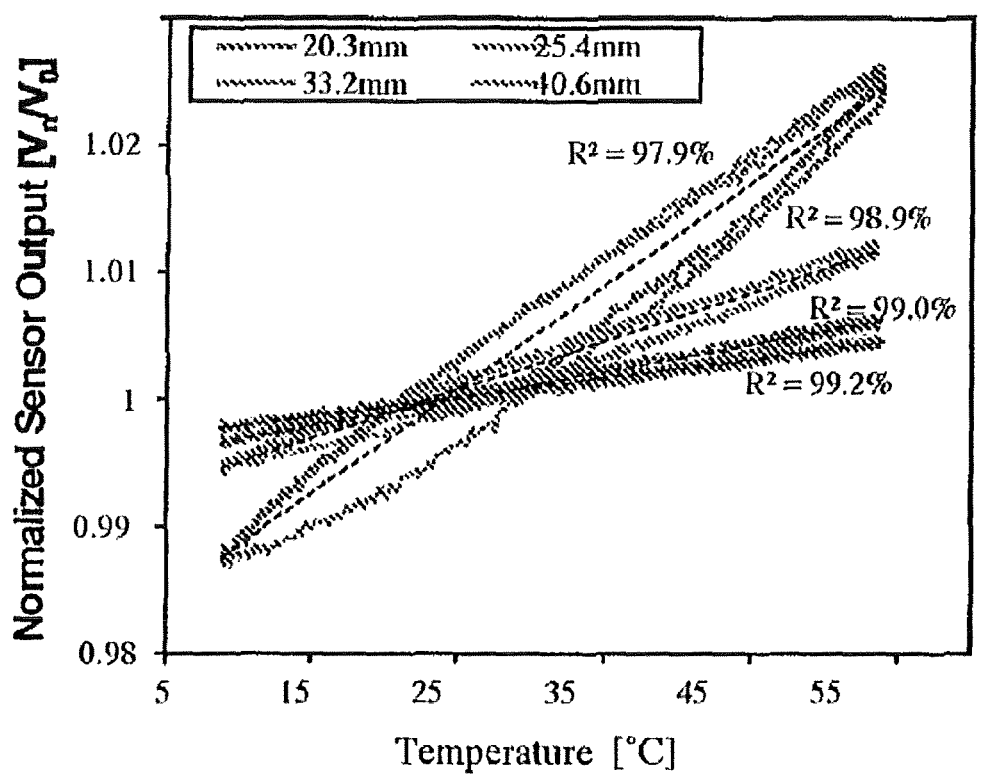
FIG. 5A shows a graph for normalized sensor output vs. temperature.
Figure 5B:
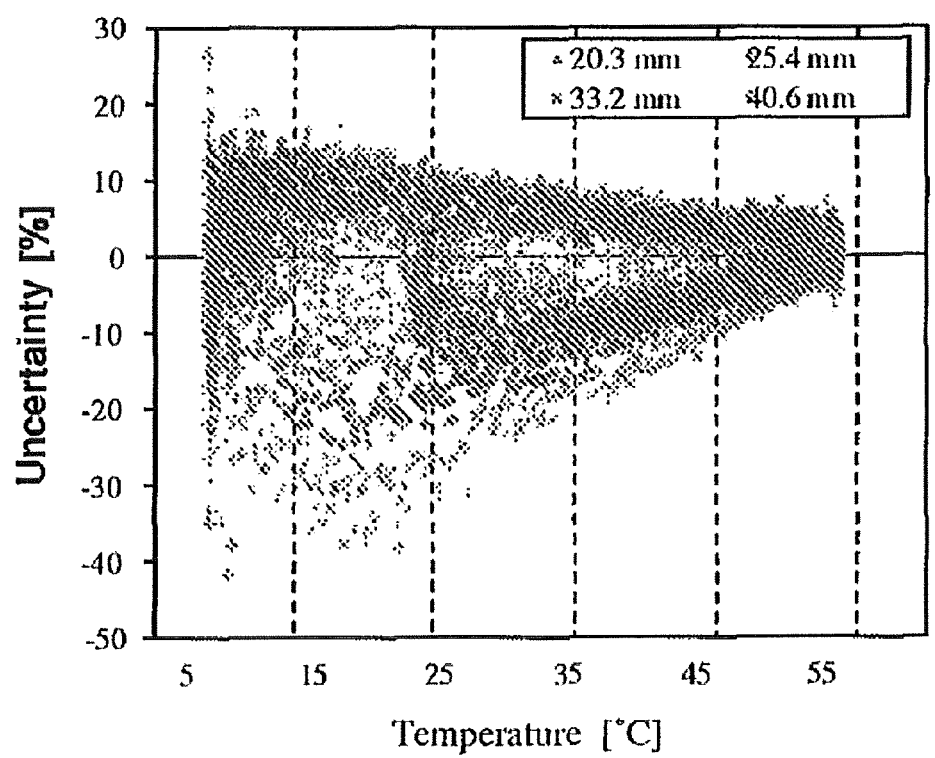
FIG. 5B shows the uncertainty in the measured temperature against actual temperatures derived using the linear curve fit equations.

The graph for normalized sensor output vs. temperature is shown in FIG. 5A. The sensor output varied linearly with temperature from 7° C. to 54° C. The ring magnet 22 was rated for temperatures below 0° C. but the measurement range was limited by the minimum temperature range of the hot-cold plate. The curve fit results are also shown in FIG. 5A. The curve fit ($R^2$) values were above 97% indicating excellent linear response of Hall sensor 24 output with temperature. FIG. 5B shows the uncertainty in the measured temperature against actual temperatures derived using the linear curve fit equations. For distances less that 40.6 mm, some hysteresis was observed in the sensor output. These responses were similar to typical B—H curve of magnets. In a magnet B—H curve, the highest hysteresis is observed at central portion of the graph near the magnetization/demagnetization regions. At the saturation points the hysteresis reduces. Similar effect was observed in these results. The uncertainty was highest at low temperatures, ranging from +20% to −35%. Another reason for high uncertainty at low temperatures was constant 1.2° C. error introduced by the reference thermocouple.

As this error was severe at low temperatures, the uncertainty in measured temperature was high. At high temperatures beyond 40° C., maximum data points were confined within uncertainty values of ±10% which is encouraging as this sensor's primary application is to detect the failure in bearings due to high temperatures. Beyond 40.6 mm distance, the inherent Hall Effect sensor output noise and variation began affecting the measurement thus introducing errors in the measurement. In the FIG. 5B plot, as many data points crossed uncertainty value of −40% for 40.6 mm plot indicating inherent Hall Effect sensor noise. Thus, 40.6 mm is the maximum distance suitable for this magnet and the bearing.

Figure 6:
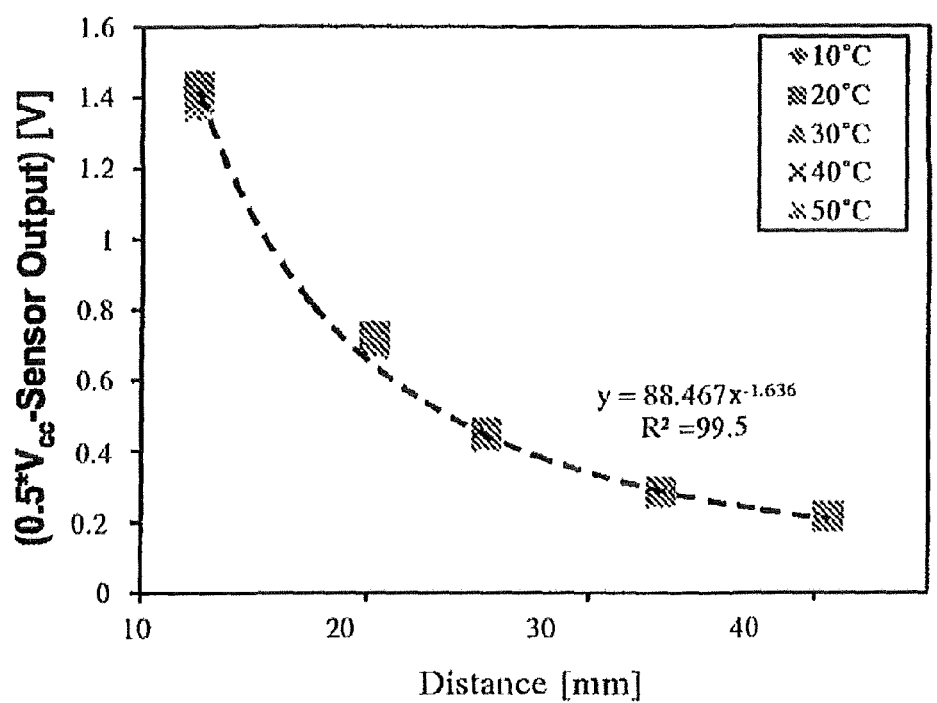
FIG. 6 shows sensor output vs. distance plotted at various temperatures.

FIG. 6 shows sensor output vs. distance plotted at various temperatures. The magnetic field intensity at a particular distance from the magnet is function magnet geometry, surrounding material's permeability, and the point at which magnetic field is measured with respect to the magnet. In some applications, the field intensity is proportional to $1/d^2$ where d is the distance between the magnet and the Hall Effect sensor. In this case, the relation was $88.47*(1/d^{16})$ obtained from measurement results shown in FIG. 6. The power value was less than the ideal relationship, perhaps due to two reasons. Firstly, presence of magnetic bearing that affects the fields, secondly for a ring magnet; the field is preferably measured at the center. In this case, the field was measured at the edge of the magnet.

B. Effect of Various Metal Plates Between Magnet and Hall Effect Sensor

Wireless sensors for bearing temperature monitoring, presented in and suffer from Eddy current losses and signal attenuation due to presence of the metals in close proximity. A majority of rotating machines are constructed using stainless steel. Stainless steels are available in various grades depending on the quantity of chromium, nickel or other corrosion reducing, hardening materials present in the alloy. In some applications, this composition varies from 10% to 20%.

Due to this and the type of fabrication process used, the magnetic domains are not set in 300 series stainless steel grades, thus making them almost non-magnetic. These stainless steels are known as Austenitic stainless steel. To study the capability of the magnet and Hall Effect sensor to penetrate non-magnetic metal plates, another hot plate test was carried out. In this test, the distance between the magnet 22 and the Hall Effect sensor 24 was fixed at 26 mm. Two 9.5-mm thick aluminum, copper and 304 grade austenitic stainless steel metal plates were placed between the Hall Effect sensor 24 and the magnet 22 on the bearing 12.

Figure 7A:
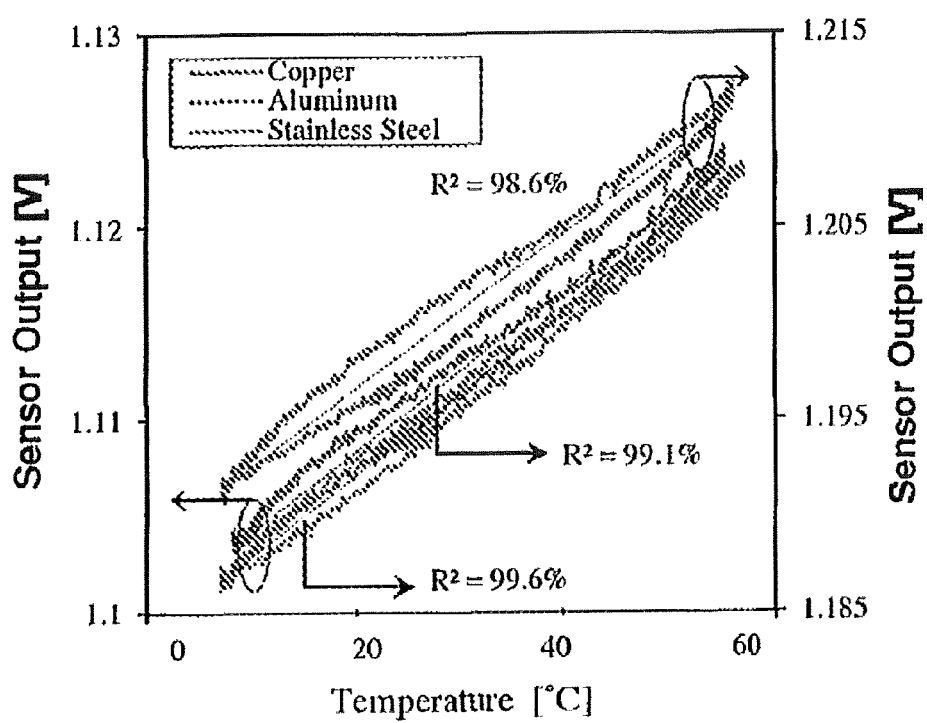
FIG. 7A shows a plot that illustrates Hall Effect sensor output vs. temperature in the presence of different types of metal plates.
Figure 7B:
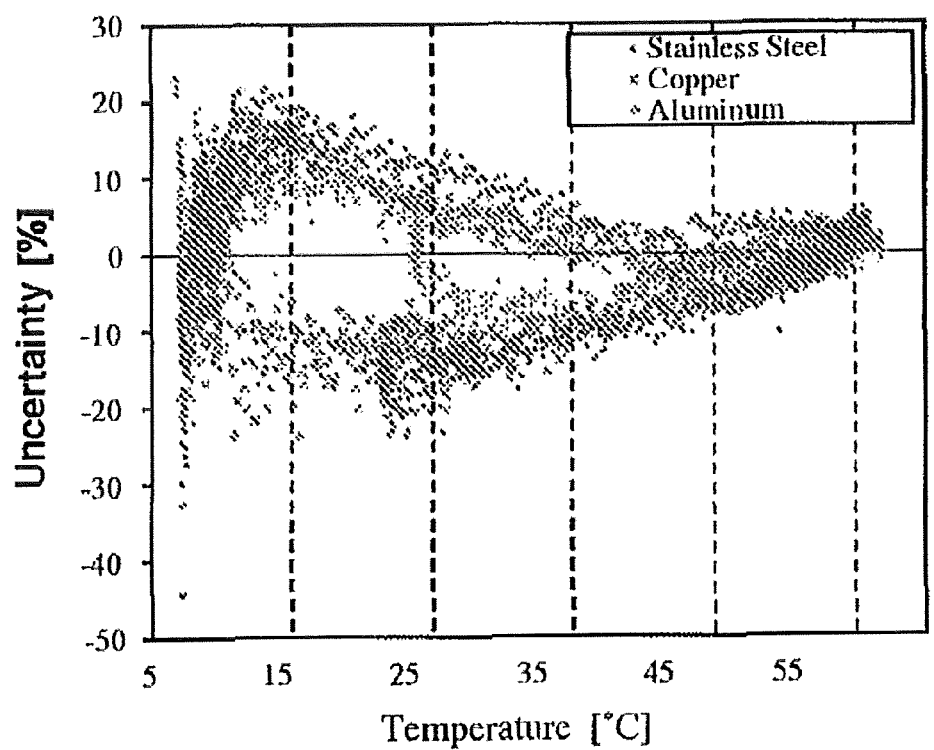
FIG. 7B shows a plot that illustrates uncertainty the measured temperature with respect to actual temperature.

FIG. 7A shows a plot that illustrates Hall Effect sensor output vs. temperature in the presence of different types of metal plates. The sensor output was higher with the stainless steel plate because of slight magnetic nature of the material. FIG. 7B shows a plot that illustrates uncertainty the measured temperature with respect to actual temperature. The uncertainty values were within ±20% for the three materials. The uncertainty value was almost constant even in the presence of slightly magnetic austenitic stainless steel. The uncertainty plots were similar to the results shown in FIG. 5B The curves of FIGS. 7A and 7B showed some hysteresis similar to plots shown in FIGS. 5A and 5B. The plots demonstrated excellent curve fit value of more than 96%. The field lines were able to penetrate the metal plates and reach Hall Effect sensor 24. In case of stainless steel, the measured Hall Effect sensor output was slightly greater than that of copper and aluminum which indicated dispersion of magnetic field lines. This was possibly due to presence of iron in the stainless steel and high permeability of the material as compared to copper and aluminum.

C. Response Time Measurement

The instantaneous failures in bearings are more severe as compared to long term failures as there is no prior information available about the degradation of the bearings. In such scenarios, response time of the sensor to sudden change in temperature of the bearing 12 plays a role in failure detection. Magnetic materials like NdFeB, SmCo are poor thermal conductors. Hence the dimension and the type of protective coatings used, become parameters for temperature sensing applications. The magnets 22 should be thin allowing for uniform heating in minimum time. Achieving small thickness is difficult in production and smaller thickness makes these magnets susceptible to breakage during handling.

Also, the magnetic field strength, which is proportional to the magnet dimensions, is lower for thin magnets thus, reducing the signal strength that can be sensed by the Hall Effect sensor 24. For this application, the neodymium magnet 22 was coated with 14-20 µm nickel-copper-nickel coating for corrosion protection and thickness of 6.35 mm. For response time measurement, the magnet 22 was directly placed on the hot-cold plate. The Hall Effect sensor 24 was mounted at a height on 2.5 cm from the magnet. The response time of the temperature sensor 22, 24 configuration was determined for various temperature increase rates. The sensor 22, 24 was able to respond to temperature rise rate of 0.1° C./s. The sensor output closely followed the temperature rise plot. This test was limited by the maximum temperature rise rate of the hot-cold plate which was 0.1° C./s.

Load variation and shaft misalignment on the bearing inner race 14 can lead to localized heating and in-turn localized degradation of the bearing 12. This localized failure is generally detected using visual inspection in the prior art, as localized heating leads to spot burning and blackening of these locations. In the case of bearings that are visually inaccessible, multiple thermocouples attached to the periphery can indicate localized failure. Accuracy of this method is limited by the number of thermocouples that can be used along the outer periphery of the bearing. Shaft misalignment leads to spot burning of the inner race 14. Some prior art sensors are designed for use in bearing cage temperature monitoring. These sensors were attached to the bearing cage as the cage speed was lower than the shaft speed. These sensors had a single temperature sensitive capacitor that resulted in shift in the resonant frequency that was measured externally. For localized heat detection, multiple capacitive elements are needed with different resonant frequencies. This results in non-uniform structure throughout the circumference of the bearing in the sensor system. Hence, these sensors are not suitable for inner race due to bearing balancing at high speeds. The magnetic sensor 22, 24 of at least some embodiments of the present invention provides a unique solution to this issue.

In particular, the uniform shape of the magnet 22 throughout its circumference ensures that bearing 12 is balanced while operating at high speeds. Localized heat spots will result in different temperature regions on the surface of the magnet 22 resulting in variation in the magnetic field along the circumference of the ring magnet 22. To study the ability of the sensor system to detect localized hot spots, a test setup creating localized heating was implemented. The bearing 12 was placed horizontally on the hot plate such that half of the bearing 12 was heated. Two Hall Effect sensors were used to emulate a rotating bearing 12 with a single sensor 24 detecting change in the magnetic field 22 due to temperature at fixed distance. The first sensor was facing the heated side and second sensor was facing the unheated side of the bearing. A thermocouple was placed on both sides of the bearing for reference temperature measurement. The distance between the bearing and the magnet was set at 40.6 mm.

Figure 8:
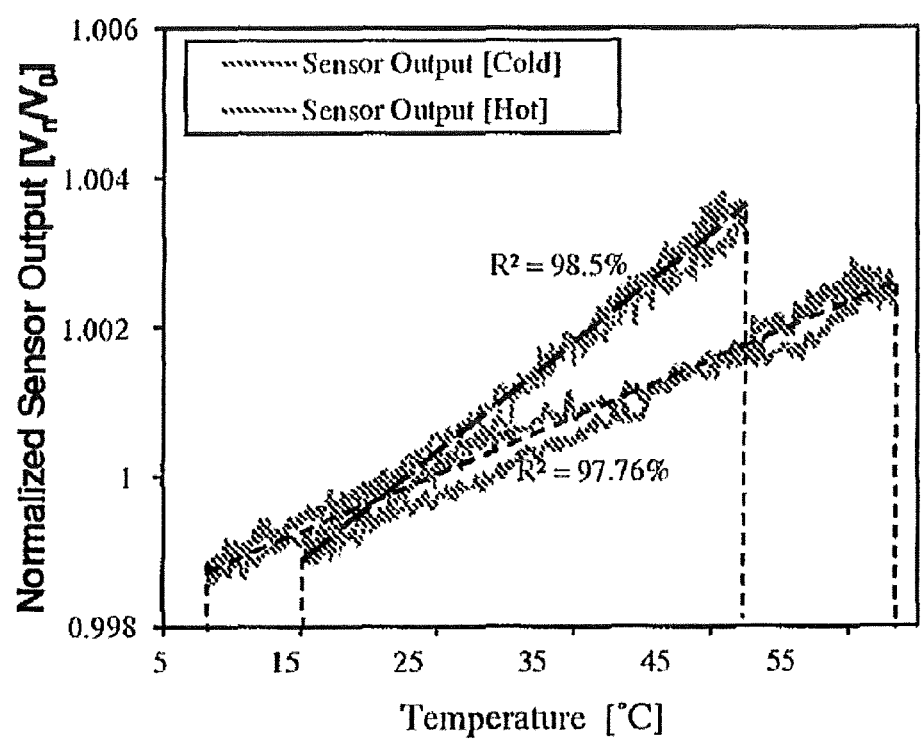
FIG. 8 shows the measurement result for localized heating test setup.

FIG. 8 shows the measurement result for localized heating test setup. Both the sensor outputs responded linearly with respect to temperature. The trends were similar to plots shown in FIG. 5A. The slope of both the curves should be same, but due to piece to piece variation in sensitivity of the Hall Effect sensors the slope of the curves was different. Of interest, was the region covered by the individual trends. The unheated side trend line varied from 15° C. to 45° C. while the heated side trend line varied from re to 56° C. indicating variation in magnetic field around the circumference of the magnet due to temperature. These results were encouraging as this sensor configuration was able to distinguish between cold and hot side of the bearing using same monolithic ring magnet. In case of practical implementation of the sensor for localized heat detection, the two Hall Effect sensors will be replaced by a single Hall Effect sensor 12 placed at a fixed distance.

E. Permanent Magnet Lifetime

One of the known properties of the magnets is the loss of the magnetic field over time. To quantify short term loss in the magnetic field, the sensor 22, 24 was subjected to 18 temperature cycles over a period of 19 hours. No appreciable magnetic field loss was observed. The linear curve fit showed the loss of 13 ppm/hr in the Hall Effect sensor output, which is small. This loss also takes into account the loss in Hall Effect sensor output due to thermal drifts, as semiconductor devices such as Hall Effect sensor 24 are affected by temperature changes and temperature drifts with time associated with hot-cold plate. Generally the loss in the magnetic field depends upon the type of material used, coercivity, permeance coefficient and operating temperature. As long as operating temperature is significantly lower than the Curie temperature with high coercivity and permeance coefficient the loss in the magnetic field over time due to temperature, is low.

Figure 9A:
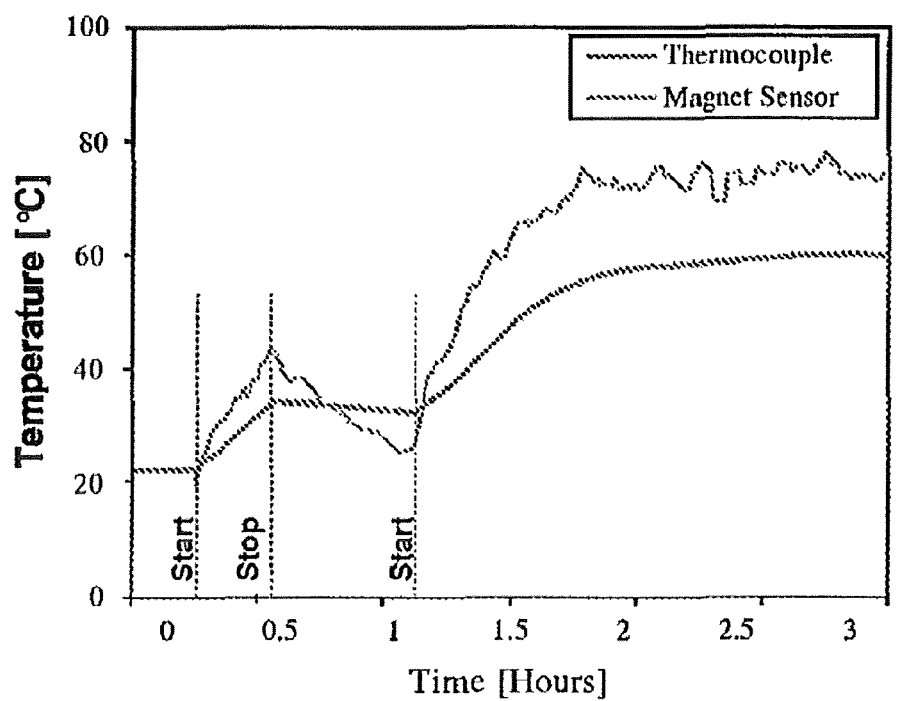
FIG. 9A shows a time based response of the magnet sensor in comparison to outer race thermocouple for first three hours of operation of a bearing test rig.
Figure 9B:
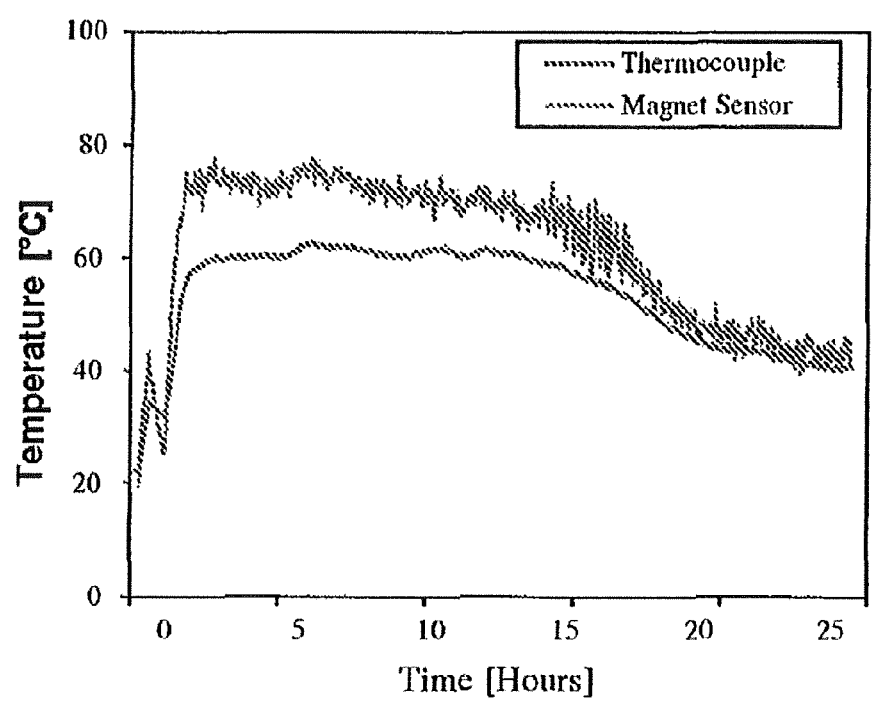
FIG. 9B shows a time based response of the magnet sensor in comparison to outer race thermocouple for continued testing of the sensor for 24 hours up to a temperature steady state condition.

Losses for various grades of neodymium magnets have been characterized. These magnets produced about a 2% loss in their magnetic field after 10000 hours at both 80° C. and 150° C. This proves that, permanent magnets can be implemented for temperature sensor applications in failure detection systems for long durations without any loss in magnetic field. Any small discrepancy introduced in the measurements due to magnetic field loss with time can be corrected using advanced software Dynamic Testing The sensor 22, 24 was tested on an actual rotating bearing test rig with the magnet 22 and Hall Effect sensor 24 mounted on the bearing 12. A thermocouple was mounted close to the periphery of the bearing 12 to measure the outer race temperature for purposes of comparison. FIG. 9A shows a time based response of the magnet sensor in comparison to outer race thermocouple for first three hours of operation. The sensor responded effectively to the transient condition such as starting and stopping of the rig. FIG. 9B shows a time based response of the magnet sensor in comparison to outer race thermocouple for continued testing of the sensor for 24 hours up to a temperature steady state condition.

For dynamic testing, N42SH grade ring magnet 22 with the same dimensions was used. N42SH grade magnets are high temperature grade magnets specified up to 150° C. The distance between the magnet 22 and Hall Effect sensor 24 was approximately 14 mm while distance between the ferromagnetic shaft and the Hall Effect sensor 24 was 3 mm. Based on the magnetic field measured at this location, and modification of the magnetic field pattern by the magnetic shaft, the calibration equation was modified to incorporate a constant temperature offset which was equal the difference between the temperature measured by the outer race thermocouple and magnet sensor at start of the test (room temperature). The testing was performed at 1500-2000 rpm and 100-150 lb load for 24 hours. As shown in FIG. 9A, the outer race (thermocouple) temperature is not a true indicator of bearing temperature. The response of the magnet wireless sensor 22, 24 was faster as compared to the thermocouple even for transient conditions such as starting and stopping of the test rig.

In this application presented an innovative concept of using a permanent magnet to implement a wireless temperature sensor 22, 24 for bearing condition monitoring in a metallic environment. The sensor presented was able to measure temperature remotely from a distance of 40.6 mm which is the greatest distance ever reported for a wireless bearing condition monitoring system. The sensor was able to measure change in the magnetic field due to temperature through a 19-mm thick stainless steel plate using a Hall Effect sensor. A ring magnet 22 presents a viable solution to localized heating detection on bearing inner race with a geometry that will not affect the bearing balance at high speeds. Furthermore, the dynamic tests on the test rig showed the effectiveness of this sensor in detecting the temperature of the inner race without any active components mounted on the bearing while simultaneously proving the ineffectiveness of outer race thermocouple as true indicator of bearing temperature.

The embodiment described above also presents a wireless temperature sensor 22, 24 operating in an enclosed metallic environment using permanent rare earth magnets. The sensor is based on change in magnetic field with temperature which is detected using commercially available Hall Effect sensors. Temperature of a hot plate at a distance of 19 mm in air and through a 9.5-mm thick non-magnetic austenitic stainless steel plate is successfully detected from 5° C. to 80° C. as a proof-of-concept demonstration. The curve fit values showed excellent response with R2 value greater than 98% for both the cases.

The Allegro A1395 Hall Effect sensor with sensitivity of 10 mV/G was selected for implementation of this concept. The A1395 Hall Effect sensor has a small footprint of 6 mm2 along with ratio-metric output depending on the magnet pole facing the sensor.

Figure 10:
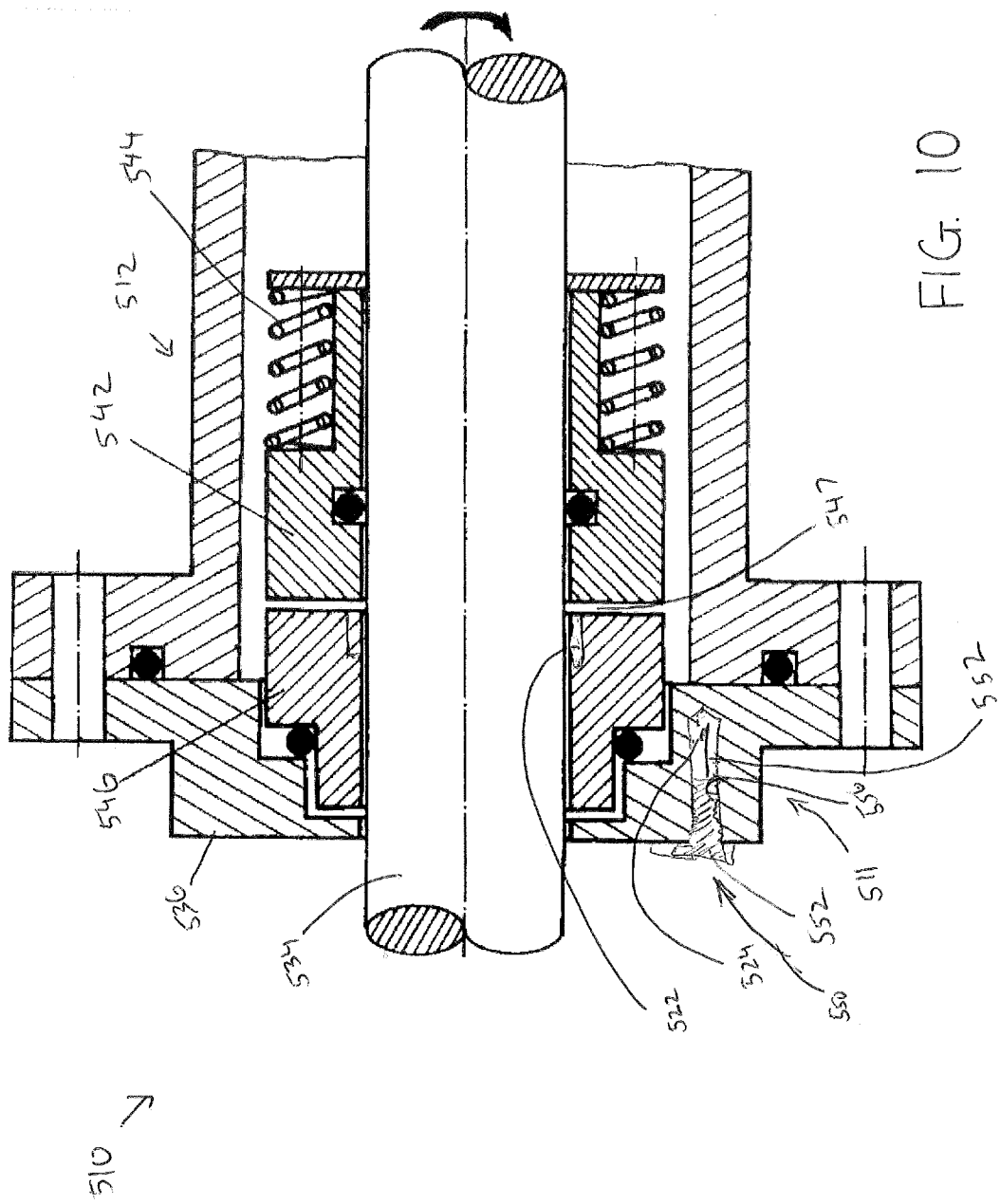
FIG. 10 shows a cutaway of an arrangement for measuring conditions of a mechanical face seal.
Figure 11:
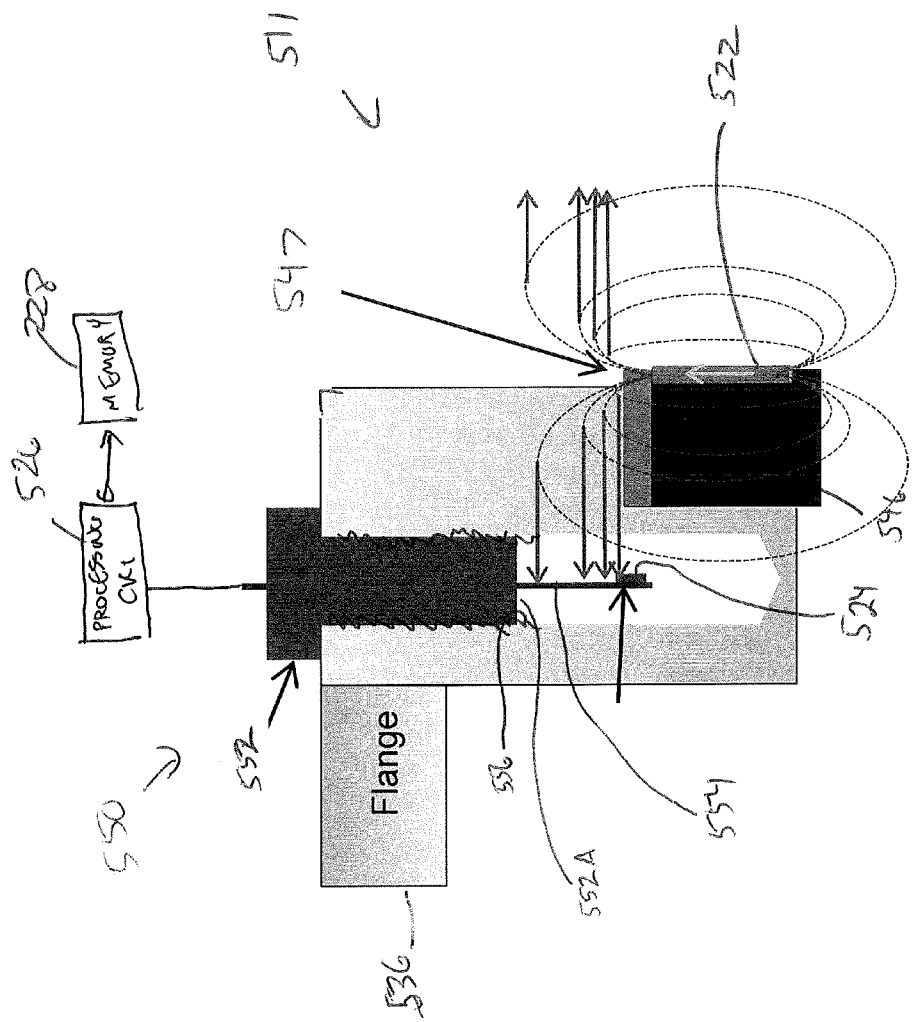
FIG. 11 shows schematically an enlarged fragmentary view of the arrangement of FIG. 10.

FIGS. 10 and 11 show another embodiment of the invention in the form of an arrangement 510 for measuring at least one aspect of a mechanical face seal 512. The arrangement 510 includes the mechanical face seal 512, and a measurement system 511. FIG. 10 shows a cutaway of the arrangement 510 and FIG. 11 shows schematically an enlarged fragmentary view of the arrangement 510.

The measurement system 511 includes a permanent magnet 522, a magnetic sensor 524, a processing circuit 526, and a memory 528. In the arrangement 510 of FIGS. 10 and 11, the mechanical face seal 512 is part of a pump subsystem that includes shaft 534 that is sealed against a flange 536. The general structure of the pump subsystem, the shaft 534, the flange 536 and many of the structures of the mechanical face seal 512 are conventional. The mechanical face seal 512 includes a rotor 542, a rotor spring 544, a stator 546.

In accordance with the present embodiment of the arrangement 510, the permanent magnet 522 is disposed within the stator 546 adjacent or proximate to the interface 547 between the rotor 542 and the stator 546. It is at this interface 547 that the friction heat of the operation of the mechanical face seal 512 is borne. In general, the rotor 542 rotates with the shaft 534 and the stator 546 remains stationary with the flange 536. The bearing surface therebetween creates the heated interface 547. Accordingly, the permanent magnet 522 is disposed adjacent to this location 547, within the stator 546. To this end, the permanent magnet 522 may suitably be a cylinder or half-cylinder shaped magnet having opposing ends of the cylinder as its two magnetic poles. In this embodiment the longitudinal or axial direction (which is also the magnetization direction) of the permanent magnet 522 is substantially parallel to the axis of rotation of the shaft 534. In this embodiment, the permanent magnet 522 is disposed and secured (via adhesive or the like) in a hole drilled in stator 546.

The magnetic sensor 524, which in this embodiment is a Hall effect sensor, is mounted within or around the flange 536 in proximity to the permanent magnet 522. The sensing surface 524a of the Hall effect sensor 524 is preferably oriented such that it is normal to at least some components of the radiating magnetic fields of the permanent magnet 522, illustrated by flux lines 548. Thus, in this embodiment, the sensing surface 524a of the magnetic sensor 524 is a surface running substantially parallel to the axial direction of the of the permanent magnet 522, and is also offset in the axial direction from the nearest end of the permanent magnet 522.

As shown in FIG. 11, the magnetic sensor 524 is part of a sensor assembly 550 that includes a housing 552, a circuit board 554, and the magnetic sensor 524. The housing 552 may take the form of a hollow, threaded bolt configured to be rotatably received by a corresponding threaded opening 556 of the flange 536. The circuit board 554 is operably supported by the housing 552, and extends outward from a distal end 552A of the housing 552. The magnetic sensor 524 is mounted on a surface of the circuit board 554 that faces the permanent magnet 522, on the portion of the circuit board 554 that extends past the distal end of the housing 552.

The threaded opening 556 is a bore within the flange 536 that has a length that accommodates the housing 522 and the entire circuit board 554 that extends therefrom. The threaded opening 556 rotatably receives the housing 522 such that the housing 522 and the circuit board 554 are fully within the bore 556. In such a position, the magnetic sensor 524 can sense the magnetic field generated by the permanent magnet 522. The magnetic sensor 524 is further operably coupled to the processing circuit 526 and the memory 528, which may suitably be configured to carry out the same signal analysis operations as those discussed above in connection with FIG. 2.

During use of the mechanical face seal 512, the friction between the rotor 542 and the stator 546 creates heat, which affects the magnetic field of the permanent magnet 522. The magnetic sensor 524 detects the change in the magnetic field in the same manner as the magnetic sensor 24 of FIG. 1. The magnetic sensor 524 provides a sense signal representative of the detected magnetic field to the processing circuit 526. The processing circuit 526 then stores information representative of the temperature, based on further processing of the sensed signal, in the memory 528. In general, the processing circuit 526 may suitably perform any of the functions discussed above in connection with FIGS. 1 and 2 on the sense signal from the magnetic sensor 524. Thus, for example, the processing circuit 526 may also employ circuitry and/or functions that detect both heat information and vibration information, as discussed above in connection with FIG. 2.

Experimental data for the device of FIGS. 10 and 11 has shown the efficacy of this measurement method. It is noted that the ability of the magnetic sensor 524 to sufficiently detect the magnetic field of the permanent magnet 522 through the metallic portions of the mechanical face seal 512 are advantageous because it allows the actual heat sensing mechanism, the permanent magnet 522, to be disposed directly adjacent to the most thermally affected portion of the mechanical seal face 512. Specifically, other types of sensors have to be located on parts having less accurate temperature measurements in order to obtain communication from the sensor.

Experimental Results

Experiments were conducted on a wireless temperature sensor 522, 524 operating through metal enclosure for mechanical face seal applications. The sensor 522, 524 is based on temperature-induced magnetic field change in permanent magnets sensed remotely by a Hall Effect sensor. The sensor 522, 524 has been tested from 5° C. to 78° C. and has shown excellent linear results with curve fit value of 98%. The sensor concept is verified by performing dynamic tests at 1800 rpm and 12 bar pressure using water as system fluid in a seal test rig. The sensor response was compared to a prior art thermocouple attached to the seal stator where excellent agreement is obtained.

Permanent magnetism is a result of microscopic domain alignment along particular direction in magnetic materials. This alignment is temperature dependent resulting in lower fields at higher temperatures. The temperature-induced magnetic field loss is highly repeatable for magnet with high coercivity and high permeance coefficient. Coercivity is a magnet's ability to oppose demagnetization in presence of external opposing magnetic fields, while permeance coefficient is a loadline on magnet's demagnetization curve. A high permeance coefficient is required to limit permanent magnetic field losses at high temperature. Permanent magnets are commercially available in various sizes and shapes and are subdivided in multiple grades depending on material, temperature range and energy content. For this application, a L38EHT grade neodymium magnet was selected as the permanent magnet 522. These magnets are rated up to 200° C. with coercivity of 2388 KOe and magnet energy product of 38 MGOe.

In the present embodiment, the magnetic sensor 524 is a Micronas HAL825 Hall Effect sensor. This sensor 524 has a programmable sensitivity of 70 mV/G and 5 V supply. The small size, minimum external signal processing circuitry and operating temperature range of 150° C. makes this sensor ideal for mechanical seal temperature sensing applications.

A semi-cylindrical slot with 2.4-mm radius and 9.5-mm length was drilled in the silicon carbide seal stator 546. The L38EHT custom made semi-cylindrical magnet 522 of 2.2-mm diameter and 9.5-mm length was attached to this slot using temperature conductive adhesive. The magnet 522 was annealed at 110° C. for 1 hour to minimize potential effect of any unstable magnetic domains before assembly.

The Hall Effect sensor 524 was mounted on a small 4.7-mm wide, 0.8-mm thick printed circuit board ("PCB") 554. Three conductive wire leads were attached to the PCB 554 for power supply, ground and output. The sensor PCB 554 is mounted on the threaded holder (housing 552) as shown in FIG. 11. The housing 552 in this embodiment comprises a 7/16-14, 25.4-mm long, 316-grade non-magnetic stainless steel screw with a 5-mm wide slot formed therein. The sensor PCB 554 is attached in the 5-mm slot using an adhesive.

This assembly 550 is coated with an insulating transparent conformal coating for operation in the harsh environment. The threaded opening 556 in this embodiment comprises a 9.5-mm diameter hole drilled in the flange 536 as shown in FIG. 11 to rotatably receive the Hall Effect sensor 524 and the sensor housing 552, thus fixing the position of the sensor 524 with respect to the magnet 522. The orientation of the field lines is shown in FIG. 11. The Hall Effect sensor 524 is subjected to lateral field lines close to the magnet south pole. This arrangement ensures that the magnet 522 has its longest dimension along its length with minimum interference to the rotating shaft 534.

Tests were performed on a Teca hot/cold plate. The tests cannot be performed on commonly used ceramic hot plates as they generate their own magnetic field. In the test a prior art thermocouple was attached to the seal stator 546 for reference temperature measurement. The sensor housing 552 position was fixed using hot glue to avoid accidental rotation of the screw. The seal 512 with the flange 536, shaft 534 and sleeve were kept inverted on the hot plate to simulate the seal stator 546 in contact with the rotor in pump housing subjected to friction and heat. The hot plate was cycled from 0° C. to 90° C. with rise time, fall time and constant temperature time of 40 minutes each. The data was recorded using a multi-meter, PC and Labview code.

Figure 12:
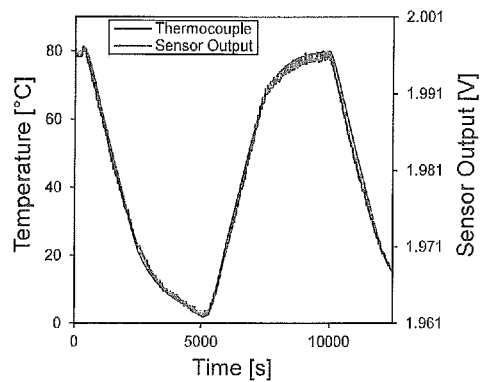
FIG. 12 shows measured temperature cycling results from 8° C. to 79° C. for the arrangement of FIG. 10.
Figure 13:
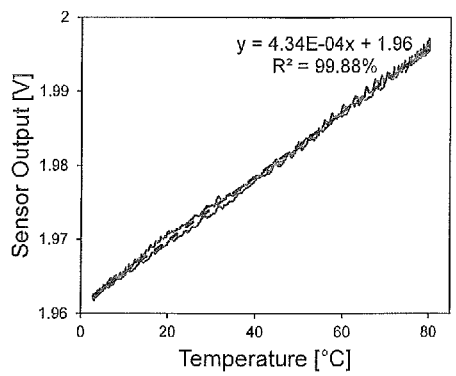
FIG. 13 shows the Hall Effect sensor output vs. seal temperature in the arrangement of FIG. 10.

FIG. 12 shows measured temperature cycling results from 8° C. to 79° C. The Hall Effect sensor 524 output closely follows the actual temperature curve. FIG. 13 shows the Hall Effect sensor 524 output vs. seal temperature. The results show excellent congruity with the linear equation with curve fit value of 98%. In other words, the processing circuit 526 in one embodiment employs a linear equation (slope and intercept) to convert the received sensor signal to a temperature value. A minor hysteresis is observed which is possibly due to the difference between the response times in magnet sensor's output and thermocouple. The upper temperature limit for the sensor 522, 524 is limited by the hot plate and the test setup and not by the magnet 522 temperature specifications.

In another test, the stationary face seal 512 was installed on a seal test rig. The distance and position of the magnet 522 and the Hall Effect sensor 524 was identical to the system configuration implemented for stationary testing, discussed above. For test purposes, a prior art thermocouple is attached to the seal stator to measure the seal reference temperature and compare the results obtained by the magnet sensor. The thermocouple data was acquired using NI-9310 thermocouple DAQ card. On-site calibration was performed by rotating the sensor holder 552 orientation and matching the Hall Effect sensor output to the voltage value at 22° C. (room temperature) measured during stationary tests. The data of the magnet sensor 522, 524 was acquired using a NI-6343 USB DAQ and applying a calibration. In this case, an offset of −6° C. was added to the calibration equation to compensate for piece-to-piece variation in the seal housing/flange and minor variations in the magnet and Hall Effect sensor 524 positioning. The tester was operated at 1800 rpm and 12 bar water pressure.

Figure 14:
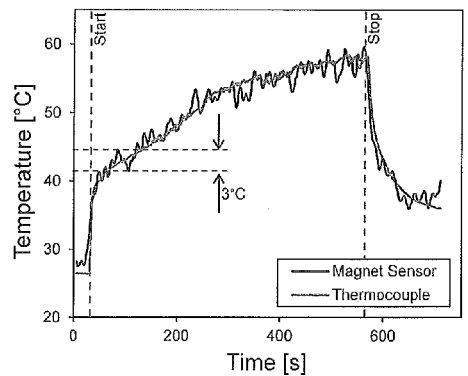
FIG. 14 shows the time based result for the magnet sensor combination and the thermocouple for the arrangement of FIG. 10.

FIG. 14 shows the time based result for the magnet sensor combination 522, 524 and the thermocouple. These results show excellent congruity. The magnet sensor combination 522, 524 is able to respond to fast transients during starting and stopping of the test rig. The noise in the magnet sensor output is due to the low resolution of the data acquisition card (16-bit ADC). This noise can be reduced with better data acquisition in a processing circuit 526 that employs a high internal ADC resolution, good amplification, and good software-based averaging and filtering. The processed measurement data with averaging shows noise induced variation of 2-3° C. in comparison to thermocouple as shown in FIG. 14.

In general, permanent magnets lose magnetic field strength with time. These losses become significant at high temperatures. The magnetic field loss depends upon the magnet type, material, coercivity, permeance coefficient and operating temperature. Coercivity is a material specific property which is difficult to control. A permeance coefficient is a geometric property that can be modified to reduce time-based magnetic field losses. For stand-alone magnets, the permeance coefficient is a function of magnet's dimensions. The magnetic field losses can be reduced significantly if magnet's length in polarization direction is greater than cross section dimensions. As discussed above, the magnet 522 preferably has a magnetization direction (between polar ends) that is along the axis of the cylinder or half-cylinder magnet 522. Magnets with permeance coefficient values greater than 3 can be used for long durations with minimal losses at high temperature.

The permeance coefficient value for a cylindrical magnet is calculated by;

$$Pc = \frac{L}{R^2}\sqrt{R+(R+L)}$$

where R and L are the cylindrical magnet's radius and length along the magnetization direction. In this embodiment, the magnet 522 geometry is semi-cylindrical. No direct theoretical equation exists for this shape. Hence, estimation is performed by assuming a cylindrical magnet with cross-section area same as the area of the semi-cylindrical magnet. Subsequently, the radius and permeance coefficient are calculated. The length is assumed to be same for semi-cylindrical and cylindrical magnet.

The estimated permeance coefficient of the semi-cylindrical magnet is 16.36. Temperature induced magnetic field losses for various grades of Nd—Fe—B magnets have been observed at 1-3% loss in the magnetic field after 10,000 hours at 80° C. and 150° C. for permeance coefficient values of 1.1 and 3.3. As such, the these magnets are suitable for this sensor 522, 524 for long durations in mechanical seals.

It will be appreciated that the above-described embodiments are merely illustrative, and that those of ordinary skill in the art may readily devise their own implementations and modifications that incorporate the principles of the present invention and fall within the spirit and scope thereof.

We claim:

1. A system for measuring a physical characteristic of mechanical face seal, comprising:

a permanent magnet affixed to a structure such that the permanent magnet has a temperature corresponding to a bearing surface of the mechanical face seal, the permanent magnet having a magnetic field that decreases as a function of temperature; and a magnetic sensor mounted on the mechanical face seal in a magnetic field sensing relationship with the permanent magnet, the magnetic sensor configured to generate a voltage signal corresponding to a sensed magnetic field.

2. The system of claim 1, wherein the permanent magnet is mounted on a stationary element of the mechanical face seal.

3. The system of claim 2, wherein the permanent magnet has a magnetization along a first direction, the first direction substantially parallel to an axial direction of a rotating shaft within the mechanical face seal.

4. The system of claim 3, wherein the permanent magnet has a half-cylinder shape.

5. The system of claim 4, wherein the magnetic sensor is mounted within a flange of the mechanical face seal.

6. The system of claim 5, wherein the magnetic sensor comprises a Hall effect sensor.

7. The system of claim 1, further comprising a processing circuit, the processing circuit configured to determine at least one vibration characteristic based on the voltage signal.

8. The system of claim 7, wherein the processing circuit is further configured to determine at least one temperature characteristic based on the voltage signal.

9. The system of claim 1, further comprising a display, and wherein the processing circuit is configured to cause the display to display information based on the determined at least one vibration characteristic.

10. The system of claim 1, further comprising a processing circuit operably coupled to the magnetic sensor, the processing circuit configured to determine temperature information based on the voltage signal, and the processing circuit configured to cause a display of the determined temperature information.

11. A mechanical seal system, comprising:

a rotor configured to rotate with a shaft, a stator configured to extend around the shaft;

an interface defined between the rotor and the stator;

a permanent magnet affixed to a structure having a heat transfer relationship with proximate to the interface, the permanent magnet having a magnetic field that decreases as a function of temperature; and a magnetic sensor mounted on the mechanical face seal in a magnetic field sensing relationship with the permanent magnet, the magnetic sensor configured to generate a voltage signal corresponding to a sensed magnetic field.

12. The mechanical seal system of claim 11, further comprising a flange disposed adjacent the stator, and wherein the magnetic sensor is mounted on the flange.

13. The mechanical seal system of claim 12, wherein the permanent magnet is mounted on the stator.

14. The mechanical seal system of claim 13, wherein the permanent magnet has a magnetization along a first direction, the first direction substantially parallel to an axial direction of a rotating shaft within the mechanical face seal.

15. The mechanical seal system of claim 14, wherein the flange is disposed within an axial bore within the flange.

16. The mechanical seal system of claim 15, wherein the magnetic sensor has a sensing surface disposed parallel to the axial direction.

17. The mechanical seal system of claim 14, wherein the magnetic sensor has a sensing surface disposed parallel to the axial direction.

18. The mechanical seal system of claim 11, further comprising a spring positioned to urge relative axial movement of the rotor toward the stator.

19. The mechanical seal system of claim 11, further comprising a sensor assembly that includes the magnetic sensor, the sensor assembly including a threaded housing that is rotatably insertable into the mechanical face seal, the magnetic sensor supported on the threaded housing.

20. A system for measuring temperature and vibration in a mechanical face seal, comprising:
- a permanent magnet coupled to at least a portion of the mechanical face seal such that the permanent magnet has a temperature corresponding to an interface in the mechanical face seal, and such that vibrations in the rotating device correspond to vibrations in the permanent magnet, the permanent magnet having a magnetic field that changes as a function of temperature; and
- a magnetic sensor operably disposed in a magnetic field sensing relationship with the permanent magnet, the magnetic sensor configured to generate a voltage or current signal corresponding to a sensed magnetic field, the magnetic sensor, the magnetic sensor affixed such that at least some of the vibrations in the rotating device that correspond to vibrations in the permanent magnet correspond to vibrations in the magnetic sensor to a lesser degree.

* * * * *